(12) United States Patent
Kshirsagar

(10) Patent No.: US 8,741,595 B2
(45) Date of Patent: Jun. 3, 2014

(54) COLIFORM DETECTION PROCESS AND KIT FOR USE THEREIN

(75) Inventor: Manjiri T. Kshirsagar, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 231 days.

(21) Appl. No.: 13/142,455

(22) PCT Filed: Dec. 29, 2009

(86) PCT No.: PCT/US2009/069629
§ 371 (c)(1),
(2), (4) Date: Jun. 28, 2011

(87) PCT Pub. No.: WO2010/078284
PCT Pub. Date: Jul. 8, 2010

(65) Prior Publication Data
US 2011/0269179 A1    Nov. 3, 2011

Related U.S. Application Data

(60) Provisional application No. 61/141,685, filed on Dec. 31, 2008, provisional application No. 61/141,813, filed on Dec. 31, 2008, provisional application No. 61/141,900, filed on Dec. 31, 2008, provisional application No. 61/267,860, filed on Dec. 9, 2009.

(51) Int. Cl.
*C12Q 1/04* (2006.01)

(52) U.S. Cl.
USPC .............................. 435/34; 502/233; 516/111

(58) Field of Classification Search
None
See application file for complete search history.

(56) References Cited

U.S. PATENT DOCUMENTS

| 3,912,593 | A | 10/1975 | Barker et al. |
| 4,036,698 | A | 7/1977 | Bush et al. |
| 4,046,712 | A | 9/1977 | Cairns et al. |
| 4,560,660 | A | 12/1985 | Geirnaert |
| 4,618,525 | A | 10/1986 | Chamberlain et al. |
| 4,698,311 | A | 10/1987 | Hall et al. |
| 4,729,846 | A | 3/1988 | Matsui et al. |
| 4,824,560 | A | 4/1989 | Alspector |
| 4,871,662 | A | 10/1989 | Rosov |
| 5,089,413 | A | 2/1992 | Nelson et al. |
| 5,119,830 | A | 6/1992 | Davis |
| 5,186,897 | A | 2/1993 | Eason et al. |
| 5,232,838 | A | 8/1993 | Nelson et al. |
| 5,238,812 | A | 8/1993 | Coulter et al. |
| 5,264,184 | A | 11/1993 | Aysta et al. |
| 5,364,766 | A | 11/1994 | Mach et al. |
| 5,403,551 | A | 4/1995 | Galloway et al. |
| 5,403,722 | A | 4/1995 | Floeder et al. |
| 5,462,860 | A | 10/1995 | Mach |
| 5,576,185 | A | 11/1996 | Coulter et al. |
| 5,681,712 | A | 10/1997 | Nelson |
| 5,759,403 | A | 6/1998 | Clauss et al. |
| 6,002,789 | A | 12/1999 | Olsztyn et al. |
| 6,021,681 | A | 2/2000 | Jezek |
| 6,045,913 | A | 4/2000 | Castle |
| 6,057,488 | A | 5/2000 | Koper et al. |
| 6,140,040 | A | 10/2000 | Palm et al. |
| 6,150,300 | A | 11/2000 | Khare |
| 6,331,429 | B1 | 12/2001 | Ushiyama |
| 6,576,193 | B1 | 6/2003 | Cui et al. |
| 6,638,755 | B1 | 10/2003 | Mizuochi et al. |
| 6,669,908 | B2 | 12/2003 | Weyker et al. |
| 6,730,230 | B2 | 5/2004 | Cook et al. |
| 6,764,969 | B1 | 7/2004 | Kuhn et al. |
| 6,861,002 | B2 | 3/2005 | Hughes |
| 6,955,099 | B2 | 10/2005 | Goodin |
| 7,022,289 | B1 | 4/2006 | Schlein et al. |
| 7,074,916 | B2 | 7/2006 | Bastian et al. |
| 7,108,662 | B2 | 9/2006 | Miller et al. |
| 7,201,841 | B2 | 4/2007 | Hughes |
| 7,298,885 | B2 | 11/2007 | Green et al. |

(Continued)

FOREIGN PATENT DOCUMENTS

| CA | 2056167 | 5/1993 |
| EP | 0093027 | 11/1983 |

(Continued)

OTHER PUBLICATIONS

Fonnum et al., Journal of Magnetism and Magnetic Materials, 2005, vol. 293, p. 41-47.*
Google, NPL search results, 2013.*
Bildirci et al., Journal of Immunological Methods, 2001, vol. 252, p. 57-62.*
Bosilevac, J.M., et al., "Prevalence of 1-15 *Escherichia coli* 0157 and Levels of Aerobic Bacteria and Enterobacteriaceae are Reduced When Hides are Washed and Treated with Cetylpyridinium Chloride at a Commercial Beef Processing Plant", *Journal of Food Protection*, vol. 67, No. 4, (Jan. 1, 2004) pp. 646-650.

(Continued)

*Primary Examiner* — Kade Ariani
(74) *Attorney, Agent, or Firm* — Adrian L. Pishko; Stephen L. Crooks

(57) ABSTRACT

A process comprises (a) providing (1) at least one sample suspected of comprising at least one coliform strain, (2) at least one culture device comprising at least one culture medium that is hydrated or hydratable, and (3) at least one particulate concentration agent that is substantially optically transparent when in contact with the culture medium in the culture device when the culture medium is hydrated; (b) placing the particulate concentration agent in contact with the sample such that at least a portion of the coliform strain is bound to the particulate concentration agent to form coliform-bound particulate concentration agent; (c) placing the coliform-bound particulate concentration agent in contact with the culture medium; (d) incubating the culture device comprising the coliform-bound particulate concentration agent in contact with the culture medium, the culture medium being hydrated; and (e) optically detecting the presence of the coliform strain without separating the coliform strain from the particulate concentration agent.

14 Claims, No Drawings

(56) References Cited

U.S. PATENT DOCUMENTS

| | | | |
|---|---|---|---|
| 7,298,886 | B2 | 11/2007 | Plumb et al. |
| 7,422,868 | B2 | 9/2008 | Fan et al. |
| 7,431,904 | B2 | 10/2008 | Høj |
| 7,496,225 | B2 * | 2/2009 | Graessle et al. ............... 382/133 |
| 8,057,688 | B2 | 11/2011 | Nonninger |
| 2001/0031491 | A1 | 10/2001 | Curtis |
| 2002/0077249 | A1 | 6/2002 | Schlegel et al. |
| 2002/0127307 | A1 | 9/2002 | McGill |
| 2003/0009014 | A1 | 1/2003 | Chiou |
| 2003/0140785 | A1 | 7/2003 | Koslos |
| 2003/0226443 | A1 | 12/2003 | Rajagopalan et al. |
| 2004/0114457 | A1 | 6/2004 | McGill |
| 2004/0127353 | A1 | 7/2004 | Wu |
| 2004/0152076 | A1 * | 8/2004 | Willson et al. ..................... 435/6 |
| 2004/0159605 | A1 | 8/2004 | Hughes |
| 2004/0178142 | A1 | 9/2004 | Koslow |
| 2004/0217061 | A1 | 11/2004 | Corzani et al. |
| 2004/0256485 | A1 | 12/2004 | Joseph et al. |
| 2005/0002970 | A1 * | 1/2005 | Ketelson et al. ............... 424/400 |
| 2005/0020449 | A1 | 1/2005 | Blais |
| 2005/0053266 | A1 | 3/2005 | Plumb et al. |
| 2005/0095189 | A1 | 5/2005 | Brey et al. |
| 2005/0244943 | A1 | 11/2005 | Ladisch et al. |
| 2006/0024776 | A1 | 2/2006 | McMillian |
| 2006/0144793 | A1 | 7/2006 | Dadachov |
| 2006/0188580 | A1 | 8/2006 | Sacks |
| 2006/0249465 | A1 | 11/2006 | Jin et al. |
| 2006/0292555 | A1 | 12/2006 | Xu et al. |
| 2007/0020649 | A1 | 1/2007 | Tseng et al. |
| 2007/0212747 | A1 | 9/2007 | Browne |
| 2008/0166792 | A1 | 7/2008 | Attar et al. |
| 2010/0190171 | A1 | 7/2010 | Kshirsagar et al. |
| 2010/0209961 | A1 | 8/2010 | Kshirsagar et al. |
| 2010/0247592 | A1 | 9/2010 | Kshirsagar et al. |
| 2010/0248214 | A1 | 9/2010 | Kshirsagar et al. |
| 2010/0248216 | A1 | 9/2010 | Halverson et al. |

FOREIGN PATENT DOCUMENTS

| | | |
|---|---|---|
| EP | 0391608 | 3/1990 |
| EP | 0 841 403 | 5/1998 |
| EP | 1524024 | 2/2010 |
| GB | 2228477 | 8/1990 |
| JP | 6-081595 | 10/1994 |
| JP | 2000-014380 | 1/2000 |
| JP | 2001-112497 | 4/2001 |
| JP | 2002-125695 | 5/2002 |
| JP | 2003-210158 | 7/2003 |
| JP | 2005-254123 | 9/2005 |
| WO | 00/23792 | 4/2000 |
| WO | 02/06791 | 1/2002 |
| WO | 02/49684 | 6/2002 |
| WO | 03/064330 | 8/2003 |
| WO | 2004/068511 | 8/2004 |
| WO | 2005/030382 | 4/2005 |
| WO | 2006/069712 | 7/2006 |
| WO | 2006/072944 | 7/2006 |
| WO | 2006/074126 | 7/2006 |
| WO | 2006/077020 | 7/2006 |
| WO | 2006/090375 | 8/2006 |
| WO | 2006/128187 | 11/2006 |
| WO | 2007/093808 | 8/2007 |
| WO | 2008/079800 | 7/2008 |
| WO | 2009/026035 | 2/2009 |
| WO | 2009/046191 | 4/2009 |
| WO | 2009/085357 | 7/2009 |

OTHER PUBLICATIONS

Grif, et al., "Dynabeads plus 3M Petrifilm HEC versus Vitek Immunodiagnostic Assay System for detection of *E. coli* 0157 in minced meat", *Letters in Applied Microbiology*, vol. 26, No. 3, (Mar. 1, 1998) pp. 199-204.

Zhu, et al., "Phase Transition between Nanostructures of Titanates and Titantium Dioxides via Simple Wet-Chemical Reaction", *J. Am. Chem. Soc.*, vol. 127, pp. 6730-6736, (2005).

US Doc. No. 4,476,226, Oct. 1984, Hansen et al. (withdrawn).

Ams et al., "Experimental measurements of the adsorption, of *Bacillus subtilis* and *Pseudomonas mendocina* onto Fe-oxyhydroxide-coated and uncoated quartz grains" Geomicrobiology Journal, vol. 21, No. 8; pp. 511-519, ISSN: 0149-0451, XP008100501, Dec. 2004.

Berry et al., "Hydroxyapatite Adherence as a Means to Concentrate Bacteria," *Applied and Environmental Microbiology*, vol. 63, No. 10, Oct. 1997, p. 4069-4074.

Brown et al., "Virus Removal by Diatomaceous-Earth Filtration-Part 1", Journal American Water Works Association, Denver, CO, vol. 66, No. 2, pp. 98-102, XP001013356, ISSN: 0003-150X, Jan. 1, 1974.

Bryant, T., "New UD Technology Removes Viruses From Drinking Water", UDaily, Office of Public Relations, University of Delaware, http://www.udel.edu/PR/UDaily/2007/feb/viruses022607.html, Feb. 26, 2007.

Chaudhuri et al., "Virus Removal by Diatomaceous Earth Filtration", Journal of Environmental Engineering Division, American Society of Civil Engineers, New York, NY, vol. 100, pp. 937-953, XP001013190, ISSN: 0090-3914, Aug. 1, 1974.

Collins et al., "Development of a rapid detection method for waterborne *Escherichia coli* 0157:H7." XP002510684 Database accession No. PREV200300556872 abstract & Abstracts of the General Meeting of the American Society for Microbiology, vol. 103, 2003, pp. Q-496 URL, 103RD American Society for Microbiology General Meeting; Washington, DC, USA; May 18-22, 2003. ISSN: 1060-2011—Database BIOSIS [Online], Biosciences Information Service, Philadelphia, PA, US; 2003.

Cullison et al. "Magnetized Carbonyl iron and Insoluble Zirconium Hydroxide Mixture Facilitates Bacterial Concentration and Separation from Nonfat Dry Milk", Journal of Food Protection, vol. 65, No. 11, pp. 1806-1810, Jun. 2002.

Dudak et al., "Determination of viable *Escherichia coil* using antibody-coated paramagnetic beads with fluorescence detection," *Anal Bioanal Chem* (2009) 393:949-956.

Farrah et al., "Adsorption of Viruses by Diatomaceous Earth Coated with Metallic Oxides and Metallic Peroxides", Wat. Sci. Tec., vol. 24, No. 2, pp. 235-240, 1991.

Farrah et al., "Adsorption of Viruses to Diatomaceous Earth Modified by In situ Precipitation of Metallic Salts", Department of Microbiology and Cell Science, University of Florida, vol. 34, No. 9, pp. 520-521, Jan. 1, 1988.

Farrah et al., "Use of Modified Diatomaceous Earth for Removal and Recovery of Viruses in Water" Applied and Environmental Microbiology, vol. 57, No. 9, pp. 2502-2506, XP001013212 ISSN: 0099-2240, Sep. 1, 1991.

Fass et al., "Silicates: non-specific adsorbents in purification of water from viruses", Pub Med, NCBI, Dev. Biol. Stand; vol. 46, pp. 91-96; 1980.

Fass et al., "Silicates as Nonspecific Adsorbents of Bacteriophage: a Model for Purification of Water from Viruses", Pub Med, NCBI, Appl. Environ. Microbial., vol. 39 (1), pp. 227-232; Jan. 1980.

Fu et al. "Anatase $TiO_2$ Nanocomposites for Antimicrobial Coatings", J. Phys. Chem. B, vol. 109, pp. 8889-8898 (2005).

Hall et al., "Sensitivity of an Immunomagnetic-Separation-Based Test for Detecting *Escherichia coli* O26 in Bovine Feces," *Applied and Environmental Microbiology*, vol. 72, No. 11, Nov. 2006, pp. 7260-7263.

Jiang et al., "Adsorption of Pseudomonoas Putida on Clay Minerals and Iron Oxide" Colloids and Surfaces. B, Biointerfaces, Elsevier, Amsterdam, NL, vol. 54, No. 2, pp. 217-221, XP005858731, ISSN: 0927-7765, Jan. 25, 2007.

Knapp et al., "The Effect of Distribution of Iron-oxyhydroxide Grain Coatings on the Transport of Bacterial Cells in Porous Media", Environmental Geology (Berlin), vol. 33, No. 4; pp. 243-248, XP002510778, ISSN: 0943-0105, Mar. 1998.

Krack et al. "Effect of Growth Phase and Metabolic Activity on the Adhesion of *Escherichia coli* K-12 AB264 to Quartz and Lepidocrocite", Geomicrobiology Journal, vol. 24, No. 3-4, pp. 179-187, XP008100479, ISSN: 0149-0451, 2007.

(56) References Cited

OTHER PUBLICATIONS

Lucore et al., "Immobilization with Metal Hydroxides as a Means to Concentrate Food-Borne Bacteria for Detection by Cultural and Molecular Methods", Applied and Environmental Microbiology, vol. 66, No. 5, pp. 1769-1776, May 2000.

Lukasik et al., "Removal of Microorganisms from Water by Columns Containing Sand Coated with Ferric and Aluminum Hydroxides", Wat. Res., vol. 33, No. 3, pp. 769-777, 1999.

Mills et al., "Effect of Solution Ionic Strength and Iron Coatings on Mineral Grains on the Sorption of Bacterial Cells to Quartz Sand", Applied and Environmental Microbiology, vol. 60, No. 9, pp. 3300-3306, XP002510777, ISSN: 0099-2240, 1994.

Rao et al., "Detection of Viruses in Drinking Water by Concentration on Magnetic Iron Oxide", Applied and Environmental Microbiology, vol. 42, No. 3, pp. 421-426, Sep. 1981.

Schindler et al., "Immobilization and Detection of Listeria Monocytogenes", Applied and Environmental Microbiology, vol. 72, No. 6, pp. 4426-4428, Jun. 2006.

Schraft et al., "Enumeration of hetertrophs, fecal coliforms and *Escherichia coli* in water: comparison of 3M™ Petrifilm™ plates with standard plating procedures," *Journal of Microbiological Methods* 60 (2005) p. 335-342.

Shah et al., "New Horizons in Purification of Liquids", Soil and Water Pollution Monitoring, Protection and Remediation, 3-23, pp. 369-386, 2006.

Stevens et al., "Bacterial Separation and Concentration from Complex Sample Matrices: A Review," *Critical Reviews in Microbiology*, 30(1):7-24, 2004.

Takeuchi et al., "High Dispersion Platinum, Catalyst by RF Sputtering," Journal of Catalysis, vol. 83, pp. 477-479, 1983.

Taylor et al., "Effect of Food Matrix and Cell Growth on PCR-Based Detection of *Escherichia coli* O157:H7 in Ground Beef", Journal of food Protection, vol. 68, No. 2, pp. 225-232, 2005.

Vail et al., "Enumeration of Waterborne *Escherichia coli* with Petrifilm Plates: Comparison to Standard Methods," *J. Environ. Qual.* 32:368-373 (2003).

Varshney et al., "Magnetic Nanoparticle-Antibody Conjugates for the Separation of *Escherichia coli* O157:H7 in Ground Beef," *Journal of Food Protection*, vol. 68, No. 9; 2005, pp. 1804-1811.

Wegmann et al., "Modification of ceramic microfilters with colloidal zirconia to promote the adsorption of viruses from water", Science Direct, Water Research 42, pp. 1726-1734, 2008.

EN ISO 9308-1:2000, "Water Quality—Detection and Enumeration of *Escherichia coli* and Coliform Bacteria,"(2000).

Lukasik, et al., "Adsorption of Microorganisms to Sand and Diatomaceous Earth Particles Coated With Metallic Hydroxides", *KONA*, vol. 14, (Jan. 1, 1996) pp. 87-91, XP055068807.

O'Brien, et al., "Bacteria Methods Comparison Study", *The Volunteer Monitor*, vol. 18, No. 1, (Jan. 1, 2006) pp. 1-24, XP0055068802.

\* cited by examiner

COLIFORM DETECTION PROCESS AND KIT FOR USE THEREIN

STATEMENT OF PRIORITY

This application claims the priorities of U.S. Provisional Applications Nos. 61/267,860, filed Dec. 9, 2009; 61/141,900, filed Dec. 31, 2008; 61/141,813, filed Dec. 31, 2008; and 61/141,685, filed Dec. 31, 2008; the contents of which are hereby incorporated by reference.

FIELD

This invention relates to processes for detecting the presence of microorganisms in test samples. In another aspect, this invention also relates to diagnostic kits for use in carrying out such processes.

BACKGROUND

In potable water testing and food safety testing, the presence or absence of coliform bacteria is considered to be important evidence of quality, and the amount of coliform bacteria permitted in drinking water and in certain foods (for example, dairy products) is regulated in many countries around the world. Coliform bacteria include fecal coliforms, such as *Escherichia coli*. The presence of fecal coliforms in a food or water sample is used as a primary indicator of fecal contamination of the food or water and of the possible presence of other pathogenic microorganisms.

Methods for detecting, identifying, and/or enumerating microorganisms in water samples can be found, for example, in the compendium *Standard Methods for the Examination of Water and Wastewater* ("SMEWW"), 21$^{st}$ Edition, which is a joint publication of the American Public Health Association, the American Water Works Association, and the Water Environment Federation. SMEWW describes a membrane filtration technique that is commonly used in water testing to obtain a direct count of the microorganisms present in relatively low concentration in relatively large volumes of water. In carrying out this technique, a certain volume of water is passed through a membrane filter, the membrane is incubated in a culture medium or device for a certain period of time, and the resulting microorganism colonies are then counted. Membrane filtration techniques are useful in monitoring the microbiological quality of samples from processes intended to produce drinking water, as well as samples from a variety of natural, unprocessed water sources.

Methods for detecting, identifying, and/or enumerating microorganisms in food samples often vary according to the nature of the food and the types of microorganisms that are likely to be found in the samples. Compendia of methods for testing food samples include *Standard Methods for the Examination of Dairy Products*, 27$^{th}$ Edition, published by The American Public Health Association, Washington, D.C., and the *Bacteriological Analytical Manual* ("BAM"), published by the U.S. Food and Drug Administration, Washington, D.C. Solid foods are usually suspended in aqueous media and mixed and/or pulverized to obtain a liquid homogenate of the food material, which can be used in methods of quantitative microbial analysis.

The above-referenced methods, however, are generally relatively expensive, involve multiple steps, and/or require relatively sophisticated instrumentation and/or relatively highly trained personnel. For example, most membrane filtration techniques require sterilized apparatus, vacuum manifolds, and manual interpretation of results. Another drawback is that membrane filters can become blocked by small particulates (for example, silt, dust, rust, or other suspended particulates).

Techniques such as centrifugation require specialized power equipment for sampling large volumes (for example, volumes greater than 50 milliliters) and require relatively extended periods of time to recover relatively low numbers of microorganisms from such volumes. Culture devices used in microbiological analysis of samples often can accommodate only relatively small sample inoculum volumes (for example, about 1 milliliter). Such limitations can be particularly problematic in the area of water testing, as U.S. Environmental Protection Agency water quality testing regulations, for example, stipulate the testing of large (100 milliliter) water sample volumes.

SUMMARY

Thus, we recognize that there is an urgent need for processes for rapidly detecting, identifying, and/or enumerating pathogenic microorganisms. Such processes will preferably be not only rapid but also low in cost, simple (involving no complex equipment or procedures), and/or effective under a variety of conditions (for example, with varying types of sample matrices and/or pathogenic microorganisms, varying microorganism loads, and varying sample volumes). In particular, we recognize that there is a need for a simple, efficient, and/or cost-effective process for coliform detection, identification, and/or quantification in test samples (for example, for use in potable water and food safety testing).

Briefly, in one aspect, this invention provides a process for detecting the presence or absence of coliform bacteria in a sample. The process comprises (a) providing at least one sample (preferably, in the form of a fluid; more preferably, a water sample) suspected of comprising at least one coliform strain;

(b) providing at least one culture device comprising at least one culture medium that is hydrated or hydratable;

(c) providing at least one particulate concentration agent that is substantially optically transparent when in contact with the culture medium in the culture device when the culture medium is hydrated;

(d) placing the particulate concentration agent in contact with the sample (preferably, by mixing) such that at least a portion of the coliform strain is bound to or captured by the particulate concentration agent to form coliform-bound particulate concentration agent;

(e) placing the coliform-bound particulate concentration agent in contact with the culture medium of the culture device;

(f) incubating the culture device comprising the coliform-bound particulate concentration agent in contact with the culture medium, the culture medium being hydrated; and (g) optically detecting the presence of the coliform strain (for example, the presence of at least one colony of the coliform strain) without separating the coliform strain from the particulate concentration agent.

Preferably, the coliform is a gas-producing coliform (more preferably, *Escherichia coli*), the culture device comprises culture medium that comprises at least one fermentable nutrient (more preferably, the culture device is a flat film culture device comprising culture medium that comprises at least one fermentable nutrient), the particulate concentration agent comprises microparticles (more preferably, inorganic microparticles), and/or the optical detection comprises detecting at least one color change (more preferably, at least one color change and the presence of at least one gas bubble proximate at least one colony of the coliform strain).

The process preferably further comprises segregating (preferably, by gravitational settling) the coliform-bound particulate concentration agent, separating the resulting segregated coliform-bound particulate concentration agent from the sample, identifying the coliform strain, and/or quantifying or enumerating a coliform concentration. The optical detection step can be either manual or automated.

It has been discovered that certain relatively inexpensive, particulate concentration agents can be effective in concentrating coliform bacteria (including, for example, relatively low levels of coliform bacteria in relatively large volume samples (for example, 100 milliliter water samples)) such that the bacteria not only remain viable for detection or assay but, surprisingly, can be optically detected or assayed (even by an automated optical detection system) in the presence of (and without the separation or removal of) the particulate concentration agent. Such particulate concentration agents can be used to concentrate the coliform strains present in a sample (for example, a food or water sample), so that one or more of the coliform strains can be more easily and rapidly assayed.

The particulate concentration agents used in the process of the invention surprisingly do not generally significantly interfere with coliform metabolism (including enzyme and/or gas production) and colony growth, or with coliform colony indicator characteristics (for example, color changes and/or gas bubbles) that are commonly relied upon for coliform detection, identification, and/or quantification. Thus, the presence of the particulate concentration agents during incubation and detection surprisingly does not generally significantly reduce the accuracy of coliform testing, including the more stringent testing required for specific identification of *E. coli* (which can be essential to maintaining public health through food and/or potable water quality testing, as explained above).

The process of the invention can provide increased sampling efficiency (for example, enabling an increase of about two orders of magnitude in sample volumes and/or a decrease of about two orders of magnitude in detectable microorganism concentrations, relative to traditional unconcentrated plating volumes of 0.1 mL) in water testing (where water samples generally contain relatively low numbers of coliform bacteria), and, through the use of particulate concentration agents, can avoid the filter clogging problems associated with the use of membrane filters for concentration. By enabling efficient sample concentration, the process can be compatible with culture devices that can accommodate only relatively small sample inoculum volumes (for example, about 1 milliliter).

The process of the invention is relatively simple and low in cost (requiring no complex equipment, expensive strain-specific materials, or highly-trained personnel) and can be relatively quickly carried out in the field (preferred embodiments enabling coliform detection within about 22 to 24 hours), without the need for the specially-equipped laboratory settings often required by more complex prior art coliform detection methods (for example, membrane filtration). In addition, the process can be effective with a variety of coliforms and with a variety of samples (different sample matrices and, unlike at least some prior art methods, even samples having low coliform content and/or large volumes). Thus, at least some embodiments of the process of the invention can meet the above-cited urgent need for low-cost, simple processes for rapidly detecting pathogenic microorganisms (especially coliforms) under a variety of conditions.

In another aspect, the invention also provides a diagnostic (or sample testing) kit for use in carrying out the process of the invention, the kit comprising (a) at least one culture device comprising at least one culture medium that is hydrated or hydratable; and (b) at least one particulate concentration agent that is substantially optically transparent when in contact with the culture medium in the culture device when the culture medium is hydrated.

DETAILED DESCRIPTION

In the following detailed description, various sets of numerical ranges (for example, of the number of carbon atoms in a particular moiety, of the amount of a particular component, or the like) are described, and, within each set, any lower limit of a range can be paired with any upper limit of a range. Such numerical ranges also are meant to include all numbers subsumed within the range (for example, 1 to 5 includes 1, 1.5, 2, 2.75, 3, 3.80, 4, 5, and so forth).

As used herein, the term "and/or" means one or all of the listed elements or a combination of any two or more of the listed elements.

The words "preferred" and "preferably" refer to embodiments of the invention that may afford certain benefits under certain circumstances. Other embodiments may also be preferred, however, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a liquid sample suspected of containing "a" target coliform can be interpreted to mean that the liquid sample can include "one or more" target coliforms.

The above "Summary of the Invention" section is not intended to describe every embodiment or every implementation of the invention. The detailed description that follows more particularly describes illustrative embodiments. Throughout the detailed description, guidance is provided through lists of examples, which examples can be used in various combinations. In each instance, a recited list serves only as a representative group and should not be interpreted as being an exclusive list.

Definitions

As used in this patent application:

"coliform strain" means a particular type of coliform bacteria that is distinguishable through a detection method (for example, coliforms of different genera, of different species within a genera, or of different isolates within a species);

"concentration agent" means a material or composition that binds microorganisms including coliforms (preferably, having a microorganism capture or binding efficiency of at least about 60 percent; more preferably, at least about 70 percent; even more preferably, at least about 80 percent; most preferably, at least about 90 percent);

"culture device" means a device that can be used to propagate microorganisms including coliforms under conditions that will permit at least one cell division to occur (preferably, culture devices include a housing to reduce or minimize the possibility of incidental contamination and/or a source of nutrients to support the growth of microorganisms);

"detection" means the identification of at least a component of a microorganism (for example, a target coliform), which thereby determines that the microorganism is present;

"genetic detection" means the identification of a component of genetic material such as DNA or RNA that is derived from a target coliform;

"immunologic detection" means the identification of an antigenic material such as a protein or a proteoglycan that is derived from a target coliform;

"microorganism" means any cell or particle having genetic material suitable for analysis or detection (including, for example, bacteria, yeasts, viruses, and bacterial endospores);

"optical detection" means identification of at least one wavelength of light that is transmitted, absorbed, emitted, reflected, refracted, scattered, or otherwise transformed (preferably, at least partially transmitted) by a culture device or medium comprising at least one microorganism or microorganism colony and that serves as an indicator or probe of the presence of at least one coliform strain (including such optical detection methods as, for example, human visual inspection, microscopic imaging, luminescence detection, fluorescence detection, other methods of analog or digital optical imaging (based, for example, on reflection, absorption, transmission, and/or luminance (preferably, at least partially transmission) measurements by an imaging device such as, for example, a camera, video equipment, or a scanner), and the like, and combinations thereof; preferred methods include human visual inspection, digital optical imaging (more preferably, digital optical imaging using a scanner), and combinations thereof);

"sample" means a substance or material that is collected (for example, to be analyzed);

"sample matrix" means the components of a sample other than microorganisms;

"substantially optically transparent" (in reference to a particulate concentration agent) means a particulate concentration agent that does not attenuate or reduce by more than 50 percent the optical detection of at least one wavelength of light ("detection wavelength") in the range of about 200 nm to about 1 micrometer (preferably, at least one visible wavelength in the range of about 400 nm to about 700 nm), relative to a corresponding optical detection in the absence of the particulate concentration agent, and thus does not prevent the use of that wavelength as an indicator or probe of the presence of at least one coliform strain (for example, the particulate concentration agent does not significantly distort or impair the observation or imaging of indicia of coliform growth (such as, for example, colony morphology, color or color change, and/or gas bubbles); preferably, the particulate concentration agent attenuates or reduces optical detection of the detection wavelength by less than or equal to about 35 percent (more preferably, less than or equal to about 25 percent; even more preferably, less than or equal to about 20 percent or about 15 percent; still more preferably, less than or equal to about 10 percent; most preferably, less than or equal to about 5 percent), relative to a corresponding optical detection in the absence of the particulate concentration agent); and "target coliform" means any coliform strain that is desired to be detected.

Sample

The process of the invention can be applied to essentially any samples suspected of containing coliforms. Coliforms are members of the Enterobacteriaceae family of bacteria and include rod-shaped, Gram-negative, non-spore forming microorganisms. Some coliforms are gas-producing microorganisms that are able to ferment lactose (to produce acid and carbon dioxide gas) when incubated (for example, at a temperature of about 35-37° C.). Coliforms can be found in the intestines of humans and animals (fecal coliforms) but can also be found in aquatic environments, in soil, and on vegetation.

The process of the invention is useful in detecting the presence of coliforms (more preferably, gas-producing coliforms; most preferably, *Escherichia coli*, about 95 percent of which are gas-producing) in samples. Coliform genera include *Escherichia, Enterobacter, Citrobacter, Klebsiella, Serratia, Shigella*, and *Hafnia. Escherichia coli* (*E. coli*) can be distinguished from most other coliforms by its growth and color reaction on certain types of culture media (for example, a color change resulting from its production of the enzyme beta-glucuronidase, which can be produced by about 97 percent of *Escherichia coli*). Since *E. coli* is almost exclusively a fecal coliform, its presence can be used as indirect evidence of fecal contamination of a sample.

Suitable samples for use in carrying out the process of the invention include, but are not limited to, medical, environmental, food, feed, clinical, and laboratory samples, and combinations thereof. Medical or veterinary samples can include, for example, cells, tissues, or fluids from a biological source (for example, a human or an animal). Environmental samples can be, for example, from a medical or veterinary facility, an industrial facility, soil, a water source, a food preparation area (food contact and non-contact areas), a laboratory, or an area that has been potentially subjected to bioterrorism. Food and/or water processing, handling, and preparation area samples are preferred, as these are often of particular concern in regard to contamination by coliforms and other bacterial pathogens.

Samples obtained in the form of a liquid or in the form of a dispersion or suspension of solid in liquid can be used directly, or can be concentrated (for example, by centrifugation) or diluted (for example, by the addition of a buffer (pH-controlled) solution). Samples in the form of a solid or a semi-solid can be used directly or can be extracted, if desired, by a method such as, for example, washing or rinsing with, or suspending or dispersing in, a fluid medium (for example, sterile water or a buffer solution). Preferably, solid or semi-solid sample can be treated either physically (for example, homogenized) and/or chemically (for example, by mixing with surfactant) to aid in suspension of its microorganisms including coliforms in a fluid medium.

Samples can be taken from surfaces (for example, by swabbing or rinsing). Preferably, the sample is a fluid (for example, a liquid, a gas, or a dispersion or suspension of solid or liquid in liquid or gas).

Examples of samples that can be used in carrying out the process of the invention include foods (for example, fresh produce or ready-to-eat lunch or "deli" meats); beverages (for example, juices or carbonated beverages); water (including potable water); biological fluids, cells, or tissues; and the like. Preferred samples include foods, beverages, water, and combinations thereof (with beverages, water, and combinations thereof being more preferred; with water being even more preferred; and with potable water being most preferred). Non-limiting examples of fluid samples that can be suitable for use in carrying out the process of the invention include surface water, water for human or animal consumption, water for biopharmaceutical preparations, food or dairy products suspended in an aqueous solvent, beverages, fruit juice, process water, rinse water, irrigation water, cooling water, circulating water, boiler water, boiler feed water, ground water, recreational water, treated water, and wastewater.

Sample volume can vary, depending upon the particular application. When the process is used for a food pathogen testing assay or for potable water safety testing, the volume of the sample can typically be in the milliliter to liter range (for example, 100 milliliters to 3 liters). In an industrial application, such as bioprocessing or pharmaceutical formulation, the volume can be tens of thousands of liters.

The use of particulate concentration agent in the process of the invention can isolate microorganisms including coliforms from a sample in a concentrated state and can also allow the separation of microorganisms including coliforms from sample matrix components that can inhibit detection procedures that are to be used. Optionally, the use of particulate concentration agent can be supplemented by other methods of microorganism concentration. For example, centrifugation or size exclusion-based filtration (including membrane filtration) can be utilized or carried out before or after use of the particulate concentration agent in carrying out the process of the invention, if additional concentration is desired.

Culture Devices

Culture devices that are suitable for use in carrying out the process of the invention include those that comprise at least one culture medium that is useful in allowing or facilitating the growth or metabolism of microorganisms including coliforms. The culture medium of the culture device can comprise at least one nutrient (preferably, at least one fermentable nutrient) to support the growth or metabolism of at least one coliform strain and, optionally, at least one indicator to facilitate detection of the strain. Preferably, the culture device is a flat film culture device (for example, comprising at least one self-supporting base film or substrate and at least one cover film or sheet).

Nonlimiting examples of nutrients that can support the growth of a variety of microorganisms include peptones, yeast extract, glucose, and the like, and combinations thereof. Specific nutrients or combinations of nutrients necessary or desirable for growing and/or identifying certain microorganisms or groups of microorganisms including coliforms are known in the art (for example, Violet Red Bile Agar (VRBA) can be used for coliform growth).

The culture medium of the culture device can further comprise, if desired, at least one selective agent (for example, a salt, a surfactant, or an antibiotic) to provide an environment that favors the growth and/or detection of target coliforms over non-target microorganisms that may be present in the sample. The culture medium also can include gelling agents. Suitable gelling agents include cold water soluble, natural and synthetic gelling agents. Nonlimiting examples of such gelling agents include guar gum, xanthan gum, hydroxyethyl cellulose, carboxymethyl cellulose, polyacrylamide, locust bean gum, algin, and the like, and combinations thereof.

The culture medium can be placed into essentially any suitable container or housing (for example, a petri dish, beaker, or flask) to reduce or minimize the possibility of incidental contamination. Preferably, the culture medium and the container or housing can be sterilized before coliform-bound particulate concentration agent is placed in contact with the culture medium.

Suitable culture devices for use in carrying out the process of the invention include those comprising a culture medium in the form of a pre-formed hydrogel matrix (for example, agar, agarose, or calcium pectinate); dry, rehydratable, flat film culture devices (for example, those described in U.S. Pat. No. 4,476,226 (Hansen et al.); U.S. Pat. No. 5,089,413 (Nelson et al.); U.S. Pat. No. 5,232,838 (Nelson et al.); U.S. Pat. No. 6,331,429 (Ushiyama); and U.S. Pat. No. 6,638,755 (Mizuochi et al.); the descriptions of which are incorporated herein by reference); culture devices having a porous support in fluid communication with an aqueous mixture; and the like; and combinations thereof.

Useful porous supports can have any of a variety of physical forms (for example, woven fabrics, nonwovens, gels, foams, meshes, scrims, frits, microreplicated films, and the like). Useful porous supports can be constructed from hydrophilic materials (for example, filter paper or glass fiber filter). Alternatively, porous supports can be constructed from a hydrophobic material that has been treated to render the material hydrophilic or that is inherently capable of transporting an aqueous solvent or solution by capillary action, for example. Preferably, porous supports will not contain materials that can be transported through an aqueous solvent and prevent the detection of target coliforms.

Preferred culture devices for use in carrying out the process of the invention include dry, rehydratable, flat film culture devices and combinations thereof 3M™ Petrifilm™ Coliform Count Plates and 3M™ Petrifilm™ E. coli/Coliform Count Plates (available from 3M Company, St. Paul, Minn.) are preferred dry, rehydratable, flat film culture devices (the latter being more preferred). These plates are sample-ready culture devices that can be used for the propagation, detection, and/or enumeration of coliforms. Additionally, the latter plates contain indicators that facilitate the identification of E. coli in a simple, one-step detection, identification, and enumeration process (through detection of at least one color change and the presence of at least one gas bubble proximate at least one coliform colony). The process of the invention, through its use of particulate concentration agents, can be particularly useful for concentrating the microorganisms in dilute, relatively large volume (for example, 100 milliliters of water) samples to a final 1 milliliter volume, which can be directly transferred to the plates using standard pipetting techniques.

Concentration Agents

General

Concentration agents suitable for use in carrying out the process of the invention include those particulate materials or compositions that can bind microorganisms including coliforms and that are substantially optically transparent (as defined above). If desired, particulate concentration agents can be pre-screened for their level of optical transparency in a particular optical detection method by determining the degree of optical detection of a selected wavelength of light that is used to probe a sample comprising particulate concentration agent and hydrated culture medium, relative to the degree of optical detection of the same wavelength when used to probe a corresponding control sample comprising hydrated culture medium without particulate concentration agent.

Depending upon, for example, the amount of particulate concentration agent to be used and/or its average particle size, it can be preferable to select a concentration agent material that does not significantly absorb light of the selected wavelength and/or that has an index of refraction that is relatively closely matched to that of the hydrated culture medium. For example, the index of refraction difference between the two can be selected to be less than about 0.2 (preferably, less than about 0.1; more preferably, less than about 0.05; even more preferably, less than about 0.02; most preferably, less than about 0.01). Preferably (especially for use in water quality testing involving relatively large sample volumes and/or relatively low coliform concentrations), the particulate concentration agents can capture or bind at least about 60 percent (more preferably, at least about 70 percent; even more preferably, at least about 80 percent; most preferably, at least about 90 percent) of the microorganisms including coliforms present in a sample, relative to a corresponding control sample without concentration agent.

Suitable particulate concentration agents include particulate inorganic materials (for example, metal oxides, metal silicates, silica, metal carbonates, metal phosphates, diatomaceous earth, surface-modified diatomaceous earth, and the like, and combinations thereof); particles comprising functional groups (for example, amine-functional glass beads); particles comprising biomolecules, fragments of biomolecules, and/or derivatives of biomolecules (for example, beads with surface-bound antibodies, proteins, or vitamins); particles bearing coatings of inorganic materials; and the like; and combinations thereof. If desired, the particles can comprise magnetic cores with surface coatings or surface-bound groups (for example, inorganic surface coatings or surface-bound biomolecules), provided that such particles can be present in sufficiently small amounts that substantial optical transparency (as described above) can be maintained.

Particulate inorganic materials, particles comprising functional groups (preferably, functional glass beads; more preferably, amine-functional glass beads), and combinations thereof are preferred, with particulate inorganic materials being more preferred. Preferred particulate inorganic materials include those selected from metal silicates (for example, magnesium silicate); silica; metal carbonates (for example, calcium carbonate); metal phosphates (for example, hydroxyapatite); metal oxide-, gold-, or platinum-modified diatomaceous earth; and combinations thereof. Metal carbonates (preferably, calcium carbonate); titanium dioxide-, gold-, or platinum-modified diatomaceous earth (preferably, titanium dioxide-modified diatomaceous earth); silica; metal phosphates (preferably, hydroxyapatite); amorphous metal silicates (preferably, amorphous, spheroidized magnesium silicate); and combinations thereof are more preferred. Amorphous, spheroidized magnesium silicate is most preferred.

Preferably, the particulate concentration agents comprise microparticles. The microparticles preferably have a particle size in the range of about 1 micrometer (more preferably, about 2 micrometers; even more preferably, about 3 micrometers; most preferably, about 4 micrometers) to about 100 micrometers (more preferably, about 50 micrometers; even more preferably, about 25 micrometers; most preferably, about 20 micrometers); where any lower limit can be paired with any upper limit of the range.

Concentration or capture using the above-described concentration agents is generally not specific to any particular strain, species, or type of microorganism and therefore provides for the concentration of a general population of microorganisms in a sample. Specific strains of microorganisms can then be detected from among the captured microorganism population using any known optical detection method with strain-specific probes.

When dispersed or suspended in water systems, inorganic materials exhibit surface charges that are characteristic of the material and the pH of the water system. The potential across the material-water interface is called the "zeta potential," which can be calculated from electrophoretic mobilities (that is, from the rates at which the particles of material travel between charged electrodes placed in the water system). Preferably, the concentration agents have a negative zeta potential at a pH of about 7.

Metal Silicates

Metal silicate concentration agents suitable for use in carrying out the process of the invention include amorphous silicates of metals such as magnesium, calcium, zinc, aluminum, iron, titanium, and the like (preferably, magnesium, zinc, iron, and titanium; more preferably, magnesium), and combinations thereof. Preferred are amorphous metal silicates in at least partially fused particulate form (more preferably, amorphous, spheroidized metal silicates; most preferably, amorphous, spheroidized magnesium silicate). Metal silicates are known and can be chemically synthesized by known methods or obtained through the mining and processing of raw ores that are naturally-occurring.

Amorphous, at least partially fused particulate forms of metal silicates can be prepared by any of the known methods of melting or softening relatively small feed particles (for example, average particle sizes up to about 25 microns) under controlled conditions to make generally ellipsoidal or spheroidal particles (that is, particles having magnified two-dimensional images that are generally rounded and free of sharp corners or edges, including truly or substantially circular and elliptical shapes and any other rounded or curved shapes). Such methods include atomization, fire polishing, direct fusion, and the like. A preferred method is flame fusion, in which at least partially fused, substantially glassy particles are formed by direct fusion or fire polishing of solid feed particles (for example, as in the method described in U.S. Pat. No. 6,045,913 (Castle), the description of which is incorporated herein by reference). Most preferably, such methods can be utilized to produce amorphous, spheroidized metal silicates by converting a substantial portion of irregularly-shaped feed particles (for example, from about 15 to about 99 volume percent; preferably, from about 50 to about 99 volume percent; more preferably, from about 75 to about 99 volume percent; most preferably, from about 90 to about 99 volume percent) to generally ellipsoidal or spheroidal particles.

Some amorphous metal silicates are commercially available. For example, amorphous, spheroidized magnesium silicate is commercially available for use in cosmetic formulations (for example, as 3M™ Cosmetic Microspheres CM-111, available from 3M Company, St. Paul, Minn.).

Amorphous metal silicate concentration agents can further comprise other materials including oxides of metals (for example, iron or titanium), crystalline metal silicates, other crystalline materials, and the like. The concentration agents, however, preferably contain essentially no crystalline silica.

Particularly preferred concentration agents suitable for use in carrying out the process of the invention include those that comprise an amorphous metal silicate and that have a surface composition having a metal atom to silicon atom ratio of less than or equal to about 0.5 (preferably, less than or equal to about 0.4; more preferably, less than or equal to about 0.3; most preferably, less than or equal to about 0.2), as determined by X-ray photoelectron spectroscopy (XPS). Such concentration agents include those described in U.S. Provisional Patent Application No. 60/977,180 (3M Innovative Properties Company), the descriptions of the concentration agents and methods of their preparation being incorporated herein by reference.

Preferably, the surface composition of the particularly preferred concentration agents also comprises at least about 10 average atomic percent carbon (more preferably, at least about 12 average atomic percent carbon; most preferably, at least about 14 average atomic percent carbon), as determined by X-ray photoelectron spectroscopy (XPS). XPS is a technique that can determine the elemental composition of the outermost approximately 3 to 10 nanometers (nm) of a sample surface and that is sensitive to all elements in the periodic table except hydrogen and helium. XPS is a quantitative technique with detection limits for most elements in the 0.1 to 1 atomic percent concentration range. Preferred surface composition assessment conditions for XPS can include a take-off angle of 90 degrees measured with respect to the sample surface with a solid angle of acceptance of ±10 degrees.

Such preferred metal silicate concentration agents can have zeta potentials that are more negative than that of, for example, a common metal silicate such as ordinary talc. Yet the concentration agents can be surprisingly more effective than talc in concentrating microorganisms such as bacteria, the surfaces of which generally tend to be negatively charged. Preferably, the concentration agents have a negative zeta potential at a pH of about 7 (more preferably, a Smoluchowski zeta potential in the range of about −9 millivolts to about −25 millivolts at a pH of about 7; even more preferably, a Smoluchowski zeta potential in the range of about −10 millivolts to about −20 millivolts at a pH of about 7; most preferably, a Smoluchowski zeta potential in the range of about −11 millivolts to about −15 millivolts at a pH of about 7).

Surface-Modified Diatomaceous Earth

Surface-modified diatomaceous earth concentration agents suitable for use in carrying out the process of the invention include those that comprise diatomaceous earth bearing, on at least a portion of its surface, a surface treatment comprising a surface modifier comprising metal oxide (preferably, titanium dioxide; other metal oxides can be utilized (alone or in combination), however, provided that such metal oxides can be present in sufficiently small amounts that substantial optical transparency (as described above) can be maintained), fine-nanoscale gold or platinum, or a combination thereof. Such concentration agents include those described in U.S. Provisional Patent Application No. 60/977,200 (3M Innovative Properties Company), the descriptions of the concentration agents and methods of their preparation being incorporated herein by reference. The surface treatment preferably further comprises a metal oxide selected from ferric oxide, zinc oxide, aluminum oxide, and the like, and combinations thereof (more preferably, ferric oxide). Although noble metals such as gold have been known to exhibit antimicrobial characteristics, the gold-containing concentration agents used in the process of the invention surprisingly can be effective not only in concentrating the microorganisms but also in leaving them viable for purposes of detection or assay.

Useful surface modifiers include fine-nanoscale gold; fine-nanoscale platinum; fine-nanoscale gold in combination with at least one metal oxide (preferably, titanium dioxide, ferric oxide, or a combination thereof); titanium dioxide; titanium dioxide in combination with at least one other (that is, other than titanium dioxide) metal oxide; and the like; and combinations thereof. Preferred surface modifiers include fine-nanoscale gold; fine-nanoscale platinum; fine-nanoscale gold in combination with at least ferric oxide or titanium dioxide; titanium dioxide; titanium dioxide in combination with at least ferric oxide; and combinations thereof.

More preferred surface modifiers include fine-nanoscale gold; fine-nanoscale platinum; fine-nanoscale gold in combination with ferric oxide or titanium dioxide; titanium dioxide; titanium dioxide in combination with ferric oxide; and combinations thereof (even more preferably, fine-nanoscale gold; fine-nanoscale gold in combination with ferric oxide or titanium dioxide; titanium dioxide in combination with ferric oxide; titanium dioxide; and combinations thereof). Fine-nanoscale gold, fine-nanoscale gold in combination with ferric oxide or titanium dioxide, titanium dioxide, and combinations thereof are still more preferred, with titanium dioxide being most preferred.

At least some of the surface-modified diatomaceous earth concentration agents have zeta potentials that are at least somewhat more positive than that of untreated diatomaceous earth, and the concentration agents can be surprisingly significantly more effective than untreated diatomaceous earth in concentrating microorganisms such as bacteria, the surfaces of which generally tend to be negatively charged. Preferably, the concentration agents have a negative zeta potential at a pH of about 7 (more preferably, a zeta potential in the range of about −5 millivolts to about −20 millivolts at a pH of about 7; even more preferably, a zeta potential in the range of about −8 millivolts to about −19 millivolts at a pH of about 7; most preferably, a zeta potential in the range of about −10 millivolts to about −18 millivolts at a pH of about 7).

The surface-modified diatomaceous earth concentration agents comprising fine-nanoscale gold or platinum can be prepared by depositing gold or platinum on diatomaceous earth by physical vapor deposition (optionally, by physical vapor deposition in an oxidizing atmosphere). As used herein, the term "fine-nanoscale gold or platinum" refers to gold or platinum bodies (for example, particles or atom clusters) having all dimensions less than or equal to 5 nanometers (nm) in size. Preferably, at least a portion of the deposited gold or platinum has all dimensions (for example, particle diameter or atom cluster diameter) in the range of up to (less than or equal to) about 10 nm in average size (more preferably, up to about 5 nm; even more preferably, up to about 3 nm).

In most preferred embodiments, at least a portion of the gold is ultra-nanoscale (that is, having at least two dimensions less than 0.5 nm in size and all dimensions less than 1.5 nm in size). The size of individual gold or platinum nanoparticles can be determined by transmission electron microscopy (TEM) analysis, as is well known in the art.

Diatomaceous earth (or kieselguhr) is a natural siliceous material produced from the remnants of diatoms, a class of ocean-dwelling microorganisms. Thus, it can be obtained from natural sources and is also commercially available (for example, from Alfa Aesar, A Johnson Matthey Company, Ward Hill, Mass.). Diatomaceous earth particles generally comprise small, open networks of silica in the form of symmetrical cubes, cylinders, spheres, plates, rectangular boxes, and the like. The pore structures in these particles can generally be remarkably uniform.

Diatomaceous earth can be used as the raw, mined material or as purified and optionally milled particles. Preferably, the diatomaceous earth is in the form of milled particles with sizes in the range of about 1 micrometer to about 50 micrometers in diameter (more preferably, about 3 micrometers to about 10 micrometers).

The diatomaceous earth can optionally be heat treated prior to use to remove any vestiges of organic residues. If a heat treatment is used, it can be preferable that the heat treatment be at 500° C. or lower, as higher temperatures can produce undesirably high levels of crystalline silica.

The amount of gold or platinum provided on the diatomaceous earth can vary over a wide range. Since gold and platinum are expensive, it is desirable not to use more than is reasonably needed to achieve a desired degree of concentration activity. Additionally, because nanoscale gold or platinum can be highly mobile when deposited using PVD, activity can be compromised if too much gold or platinum is used, due to coalescence of at least some of the gold or platinum into large bodies.

For these reasons, the weight loading of gold or platinum on the diatomaceous earth preferably is in the range of about 0.005 (more preferably, 0.05) to about 10 weight percent, more preferably about 0.005 (even more preferably, 0.05) to about 5 weight percent, and even more preferably from about 0.005 (most preferably, 0.05) to about 2.5 weight percent, based upon the total weight of the diatomaceous earth and the gold or platinum.

Gold and platinum can be deposited by PVD techniques (for example, by sputtering) to form concentration-active, fine-nanoscale particles or atom clusters on a support surface. It is believed that the metal is deposited mainly in elemental form, although other oxidation states may be present.

In addition to gold and/or platinum, one or more other metals can also be provided on the same diatomaceous earth supports and/or on other supports intermixed with the gold- and/or platinum-containing supports. Examples of such other metals include silver, palladium, rhodium, ruthenium, osmium, copper, iridium, and the like, and combinations thereof. If used, these other metals can be co-deposited on a support from a target source that is the same or different from the gold or platinum source target that is used. Alternatively, such metals can be provided on a support either before or after the gold and/or platinum is deposited. Metals requiring a thermal treatment for activation advantageously can be applied to a support and heat treated before the gold and/or platinum is deposited.

Physical vapor deposition refers to the physical transfer of metal from a metal-containing source or target to a support medium. Physical vapor deposition can be carried out in various different ways. Representative approaches include sputter deposition (preferred), evaporation, and cathodic arc deposition. Any of these or other PVD approaches can be used in preparing the concentration agents used in carrying out the process of the invention, although the nature of the PVD technique can impact the resulting activity. PVD can be carried out by using any of the types of apparatus that are now used or hereafter developed for this purpose.

Physical vapor deposition preferably is performed while the support medium to be treated is being well-mixed (for example, tumbled, fluidized, milled, or the like) to ensure adequate treatment of support surfaces. Methods of tumbling particles for deposition by PVD are described in U.S. Pat. No. 4,618,525 (Chamberlain et al.), the description of which is incorporated herein by reference. When carrying out PVD on fine particles or fine particle agglomerates (for example, less than about 10 micrometers in average diameter), the support medium is preferably both mixed and comminuted (for example, ground or milled to some degree) during at least a portion of the PVD process.

Physical vapor deposition can be carried out at essentially any desired temperature(s) over a very wide range. However, the deposited metal can be more active (perhaps due to more defects and/or lower mobility and coalescence) if the metal is deposited at relatively low temperatures (for example, at a temperature below about 150° C., preferably below about 50° C., more preferably at ambient temperature (for example, about 20° C. to about 27° C.) or less). Operating under ambient conditions can be generally preferred as being effective and economical, as no heating or chilling is required during the deposition.

The physical vapor deposition can be carried out in an inert sputtering gas atmosphere (for example, in argon, helium, xenon, radon, or a mixture of two or more thereof (preferably, argon)), and, optionally, the physical vapor deposition can be carried out in an oxidizing atmosphere. The oxidizing atmosphere preferably comprises at least one oxygen-containing gas (more preferably, an oxygen-containing gas selected from oxygen, water, hydrogen peroxide, ozone, and combinations thereof; even more preferably, an oxygen-containing gas selected from oxygen, water, and combinations thereof; most preferably, oxygen). The oxidizing atmosphere further comprises an inert sputtering gas such as argon, helium, xenon, radon, or a mixture of two or more thereof (preferably, argon). The total gas pressure (all gases) in the vacuum chamber during the PVD process can be from about 1 mTorr to about 25 mTorr (preferably, from about 5 mTorr to about 15 mTorr). The oxidizing atmosphere can comprise from about 0.05 percent to about 60 percent by weight oxygen-containing gas (preferably, from about 0.1 percent to about 50 percent by weight; more preferably, from about 0.5 percent to about 25 percent by weight), based upon the total weight of all gases in the vacuum chamber.

The diatomaceous earth support medium can optionally be calcined prior to metal deposition, although this can increase its crystalline silica content. Since gold and platinum are active right away when deposited via PVD, there is generally no need for heat treatment after metal deposition, unlike deposition by some other methodologies. Such heat treating or calcining can be carried out if desired, however, to enhance activity.

In general, thermal treatment can involve heating the support at a temperature in the range of about 125° C. to about 1000° C. for a time period in the range of about 1 second to about 40 hours, preferably about 1 minute to about 6 hours, in any suitable atmosphere such as air, an inert atmosphere such as nitrogen, carbon dioxide, argon, a reducing atmosphere such as hydrogen, and the like. The particular thermal conditions to be used can depend upon various factors including the nature of the support.

Generally, thermal treatment can be carried out below a temperature at which the constituents of the support would be decomposed, degraded, or otherwise unduly thermally damaged. Depending upon factors such as the nature of the support, the amount of metal, and the like, activity can be compromised to some degree if the system is thermally treated at too high a temperature.

The surface-modified diatomaceous earth concentration agents comprising metal oxide can be prepared by depositing metal oxide on diatomaceous earth by hydrolysis of a hydrolyzable metal oxide precursor compound. Suitable metal oxide precursor compounds include metal complexes and metal salts that can be hydrolyzed to form metal oxides. Useful metal complexes include those comprising alkoxide ligands, hydrogen peroxide as a ligand, carboxylate-functional ligands, and the like, and combinations thereof, Useful metal salts include metal sulfates, nitrates, halides, carbonates, oxalates, hydroxides, and the like, and combinations thereof.

When using metal salts or metal complexes of hydrogen peroxide or carboxylate-functional ligands, hydrolysis can be induced by either chemical or thermal means. In chemically-induced hydrolysis, the metal salt can be introduced in the form of a solution into a dispersion of the diatomaceous earth, and the pH of the resulting combination can be raised by the addition of a base solution until the metal salt precipitates as a hydroxide complex of the metal on the diatomaceous earth. Suitable bases include alkali metal and alkaline earth metal hydroxides and carbonates, ammonium and alkyl-ammonium hydroxides and carbonates, and the like, and combinations thereof. The metal salt solution and the base solution can generally be about 0.1 to about 2 M in concentration.

Preferably, the addition of the metal salt to the diatomaceous earth is carried out with stirring (preferably, rapid stirring) of the diatomaceous earth dispersion. The metal salt solution and the base solution can be introduced to the diatomaceous earth dispersion separately (in either order) or simultaneously, so as to effect a preferably substantially uniform reaction of the resulting metal hydroxide complex with the surface of the diatomaceous earth. The reaction mixture can optionally be heated during the reaction to accelerate the speed of the reaction. In general, the amount of base added can equal the number of moles of the metal times the number of non-oxo and non-hydroxo counterions on the metal salt or metal complex.

Alternatively, when using salts of titanium or iron, the metal salt can be thermally induced to hydrolyze to form the hydroxide complex of the metal and to interact with the surface of the diatomaceous earth. In this case, the metal salt solution can generally be added to a dispersion of the diatomaceous earth (preferably, a stirred dispersion) that has been heated to a sufficiently high temperature (for example, greater than about 50° C.) to promote the hydrolysis of the metal salt. Preferably, the temperature is between about 75° C. and 100° C., although higher temperatures can be used if the reaction is carried out in an autoclave apparatus.

When using metal alkoxide complexes, the metal complex can be induced to hydrolyze to form a hydroxide complex of the metal by partial hydrolysis of the metal alkoxide in an alcohol solution. Hydrolysis of the metal alkoxide solution in the presence of diatomaceous earth can result in metal hydroxide species being deposited on the surface of the diatomaceous earth.

Alternatively, the metal alkoxide can be hydrolyzed and deposited onto the surface of the diatomaceous earth by reacting the metal alkoxide in the gas phase with water, in the presence of the diatomaceous earth. In this case, the diatomaceous earth can be agitated during the deposition in either, for example, a fluidized bed reactor or a rotating drum reactor.

After the above-described hydrolysis of the metal oxide precursor compound in the presence of the diatomaceous earth, the resulting surface-treated diatomaceous earth can be separated by settling or by filtration or by other known techniques. The separated product can be purified by washing with water and can then be dried (for example, at 50° C. to 150° C.).

Although the surface-treated diatomaceous earth generally can be functional after drying, it can optionally be calcined to remove volatile by-products by heating in air to about 250° C. to 650° C. generally without loss of function. This calcining step can be preferred when metal alkoxides are utilized as the metal oxide precursor compounds.

In general, with metal oxide precursor compounds of iron, the resulting surface treatments comprise nanoparticulate iron oxide. When the weight ratio of iron oxide to diatomaceous earth is about 0.08, X-ray diffraction (XRD) does not show the presence of a well-defined iron oxide material. Rather, additional X-ray reflections are observed at 3.80, 3.68, and 2.94 Å. TEM examination of this material shows the surface of the diatomaceous earth to be relatively uniformly coated with globular nanoparticulate iron oxide material. The crystallite size of the iron oxide material is less than about 20 nm, with most of the crystals being less than about 10 nm in diameter. The packing of these globular crystals on the surface of the diatomaceous earth is dense in appearance, and the surface of the diatomaceous earth appears to be roughened by the presence of these crystals.

In general, with metal oxide precursor compounds of titanium, the resulting surface treatments comprise nanoparticulate titania. When depositing titanium dioxide onto diatomaceous earth, XRD of the resulting product after calcination to about 350° C. can show the presence of small crystals of anatase titania. With relatively lower titanium/diatomaceous earth ratios or in cases where mixtures of titanium and iron oxide precursors are used, no evidence of anatase is generally observed by X-ray analysis.

Since titania is well-known as a potent photo-oxidation catalyst, the titania-modified diatomaceous earth concentration agents of the present invention can be used to concentrate microorganisms for analysis and then optionally also be used as photoactivatable agents for killing residual microorganisms and removing unwanted organic impurities after use. Thus, the titania-modified diatomaceous earth can both isolate biomaterials for analysis and then be photochemically cleaned for re-use. These materials can also be used in filtration applications where microorganism removal as well as antimicrobial effects can be desired.

Contacting

The sample contacting step of the process of the invention can be carried out by any of various known or hereafter-developed methods of providing contact between two materials. For example, the particulate concentration agent can be added to the sample, or the sample can be added to the particulate concentration agent. A dipstick bearing particulate concentration agent can be immersed in a sample solution, a sample solution can be poured onto a film bearing particulate concentration agent, a sample solution can be poured into a tube or well bearing particulate concentration agent, or a sample solution can be passed through a filter (for example, a woven or nonwoven filter or a membrane filter) bearing particulate concentration agent.

Preferably, however, the particulate concentration agent and the sample are combined (using any order of addition) in any of a variety of containers (optionally but preferably, a capped, closed, or sealed container; more preferably, a capped test tube, bottle, or jar). Suitable containers for use in carrying out the process of the invention will be determined by the particular sample and can vary widely in size and nature. For example, the container can be small, such as a 10 milliliter container (for example, a test tube), or larger, such as a 100 milliliter to 3 liter container (for example, an Erlenmeyer flask or a polypropylene large-mouth bottle). The container, the particulate concentration agent, and any other apparatus or additives that contact the sample directly can be sterilized (for example, by controlled heat, ethylene oxide gas, or radiation) prior to use, in order to reduce or prevent any contamination of the sample that might cause detection errors. The amount of particulate concentration agent that is sufficient to capture or concentrate the microorganisms including coliforms of a particular sample for successful detection will vary (depending, for example, upon the nature, degree of optical transparency, and capture efficiency of the particulate concentration agent and upon the sample volume) and can be readily determined by one skilled in the art. For example, about 100 milligrams of concentration agent per 100 milliliters of sample can be useful for some applications. The particulate concentration agent is preferably present in an amount that is sufficient to provide a capture efficiency of at least about 60 percent while maintaining substantial optical transparency.

If desired, contacting can be effected by passing the particulate concentration agent at least once through a sample (for example, by relying upon gravitational settling over a period of, for example, about 10 minutes). Contact can be enhanced by mixing (for example, by stirring, shaking, or use of a rocking platform) such that the particles of concentration agent repeatedly pass or settle through a substantial portion of the sample. For small volumes on the order of microliters (typically less than 0.5 milliliter), mixing can be rapid such as by vortexing or "nutation," for example as described in U.S. Pat. No. 5,238,812 (Coulter et al.), the description of which is incorporated herein by reference. For larger volumes on the order of greater than or equal to 0.5 milliliters (typically 0.5 milliliter to 3 liters), mixing can be achieved by gently tumbling the particulate concentration agent and the sample in an "end over end" fashion, for example as described in U.S. Pat. No. 5,576,185 (Coulter et al.), the description of which is incorporated herein by reference. Such tumbling can be accomplished, for example, by means of a device configured to hold a test tube or other type of reaction vessel and to slowly rotate the test tube or vessel in an "end over end" manner. Contacting can be carried out for a desired period (for example, for sample volumes of about 100 milliliters or less, up to about 60 minutes of contacting can be useful; preferably, about 15 seconds to about 10 minutes or longer; more preferably, about 15 seconds to about 5 minutes).

Thus, in carrying out the process of the invention, mixing (for example, agitation, rocking, or stirring) and/or preliminary incubation (for example, at ambient temperature) of the combined sample and particulate concentration agent (for example, prior to placing coliform-bound particulate concentration agent in the culture device) are optional but preferred, in order to increase microorganism contact with the particulate concentration agent. A preferred contacting method includes both mixing (for example, for about 15 seconds to about 5 minutes) and preliminarily incubating (for example, for about 3 minutes to about 60 minutes) a microorganism-containing sample (preferably, a fluid) with particulate concentration agent. If desired, one or more additives (for example, lysis reagents, bioluminescence assay reagents, nucleic acid capture reagents (for example, magnetic beads), microbial growth media, buffers (for example, to moisten a solid sample; including, for example, the use of adsorption buffers), microbial staining reagents, washing buffers (for example, to wash away unbound material), elution agents (for example, serum albumin), surfactants (for example, Triton™ X-100 nonionic surfactant available from Union Carbide Chemicals and Plastics, Houston, Tex.), mechanical abrasion/elution agents (for example, glass beads), optical detection assay components (for example, indicator reagent or dye), and the like) can be included in the combination of particulate concentration agent and sample.

If desired, the particulate concentration agent (alone or in combination with, for example, carrier materials in the form of liquids (for example, water or oils), solids (for example, fabrics, polymers, papers, or inorganic solids), gels, creams, foams, or pastes) can be applied to or rubbed against a non-porous or porous, solid, microorganism-contaminated or microorganism-contaminatable material or surface (for example, as a method of sample collection). The sample can be thereby simultaneously collected and contacted with the particulate concentration agent in a single step.

Segregation and/or Separation

Optionally but preferably, the process of the invention further comprises segregation of coliform-bound particulate concentration agent resulting from the sample contacting step. Such segregation preferably can be achieved by relying, at least in part, upon gravitational settling (gravity sedimentation; for example, over a time period of about 5 minutes to about 30 minutes). In some cases, however, it can be desirable to accelerate segregation (for example, by centrifugation or filtration) or to use combinations of any of the segregation methods.

The process of the invention can optionally but preferably further comprise separating the resulting coliform-bound particulate concentration agent and the sample. For fluid samples, this can involve removal or separation of the supernatant that results upon segregation. Separation of the supernatant can be carried out by numerous methods that are well-known in the art (for example, by decanting or siphoning, so as to leave the coliform-bound particulate concentration agent at the bottom of the container or vessel utilized in carrying out the process).

The process of the invention can be carried out manually (for example, in a batch-wise manner) or can be automated (for example, to enable continuous or semi-continuous processing).

Incubation

The primary incubation step of the process of the invention can be initiated by placing the resulting coliform-bound particulate concentration agent in contact with the culture medium of the culture device, with the culture medium being in hydrated form during subsequent incubation. Such contacting can be effected either in the presence or the absence of the sample (preferably in the absence of the sample), depending upon whether optional segregation and/or separation step(s) have been carried out. The culture device (containing the coliform-bound particulate concentration agent in contact with the hydrated culture medium) can then be incubated for a period of time and at a temperature sufficient to enable at least one cell division to occur.

For example, incubation time periods of about 12 hours, 15 hours, or 18 hours to about 48 hours (preferably, at least about 18 hours to about 22 hours) and incubation temperatures ranging from about 35° C. to about 37° C. can be useful. Hydration of the culture medium (for example, by the addition of water or an aqueous diluent composition, which optionally can comprise sample and/or coliform-bound particulate concentration agent) can be effected either prior to or after (for example, immediately after or within a few minutes or hours after) the culture medium and the coliform-bound particulate concentration agent are brought into contact (or simultaneously therewith). The culture medium preferably remains substantially hydrated (and/or the contact is preferably substantially maintained) during the incubation period. Optionally, the coliform-bound particulate concentration agent and the hydrated or hydratable culture medium can be mixed (for example, so as to form a more homogeneous mixture of coliform-bound particulate concentration agent and hydrated culture medium).

Detection

Coliforms that have been captured or bound (for example, by adsorption) by the particulate concentration agent can be detected by essentially any desired optical detection method that is currently known or hereafter developed. Such methods include, for example, human visual inspection, luminescence detection, fluorescence detection, microscopy (for example, using a transmitted light microscope or an epifluorescence microscope, which can be used for visualizing microorganisms tagged with fluorescent dyes), other methods of analog or digital optical imaging (based, for example, on reflection, absorption, transmission, and/or luminance measurements by an imaging device such as, for example, a camera, video equipment, or a scanner), and the like, and combinations thereof. Preferred methods include human visual inspection, digital optical imaging (more preferably, digital optical imaging using a scanner), and combinations thereof.

Such optical detection of the presence of the coliform strain can be carried out (at one or more detection wavelengths at which the particulate concentration agent exhibits sufficient optical transparency to be termed "substantially optically transparent," as defined above) without separating the coliform strain from the particulate concentration agent. Thus, the analysis can be performed in the culture device (that is, in situ) after incubation of the culture device.

If desired, optical detection can be supplemented by, or incorporated into, any of a variety of known or hereafter-developed techniques (for example, immunological detection methods and genetic detection methods). The detection process following coliform capture optionally can include washing to remove sample matrix components, staining, or the like.

Optical detection can be carried out manually (for example, through human visual inspection) or can be automated. Automated optical detection systems for detecting and/or counting (enumerating or quantifying) microbial colonies in culture devices are known in the art. Such automated systems generally comprise an imaging system, an image analysis algorithm to determine a colony count, and a data management system to display and, optionally, store and manipulate the colony count data and images. An exemplary system for counting colonies on agar plates is sold by Synbiosis (Cambridge, UK) under the trade name Protocol™ and is described in U.S. Pat. No. 6,002,789 (Olsztyn et al.), the description of the system being incorporated herein by reference. Systems for counting colonies on 3M™ Petrifilm™ count plates (available from 3M Company, St. Paul, Minn.) are described in U.S. Pat. No. 5,403,722 (Floeder et al.); U.S. Pat. No. 7,298,885 (Green et al.); and U.S. Pat. No. 7,298,886 (Plumb et al.); the descriptions of the systems being incorporated herein by reference.

Typically, automated optical detection systems for counting microbial colonies detect the presence of target microorganisms by the ability of the colonies, or metabolites derived therefrom, either to absorb, reflect, emit, transmit, refract, or scatter light. Thus, the colonies can be detected optically by means such as, for example, colorimetically, fluorometrically, or lumimetrically (for example, chemiluminescence or bioluminescence).

In at least some tests for coliform bacteria, a coliform colony can be detected and tentatively identified as coliform by a change in the color of a pH indicator that is present in a culture medium comprising lactose. The color change can reflect a change in the pH of the culture medium, which can indicate that the colony produced acidic product(s) from the lactose. Thus, the colony can be presumed to be a coliform colony when such a color change is observed.

The presumed coliform colony can be confirmed as being coliform in such tests when one or more gas bubbles are observed proximate the colony. Some coliforms (including about 95 percent of $E.\ coli$) can produce gas (that is, carbon dioxide) from lactose. Such gas bubbles can be observed optically, either by visual means or by an automated system, such as the automated colony counting system described in U.S. Pat. No. 7,298,886 (Plumb et al.).

3M™ Petrifilm™ $E.\ coli$/Coliform Count Plates and 3M™ Petrifilm™ Coliform Count Plates (available from 3M Company, St. Paul, Minn.) are culture devices that, when hydrated and closed, comprise a semi-solid, lactose-comprising culture medium in continuous contact with a self-supporting film or substrate on one side of the culture medium and a cover film or sheet on the other side of the culture medium. Such flat film culture devices are particularly suitable for trapping the gas bubbles produced by a lactose-fermenting coliform microorganism.

Some culture devices provide means, such as selective and/or differential reagents, for unambiguously identifying a particular coliform strain present in the culture device. For example, 3M™ Petrifilm™ $E.\ coli$/Coliform Count Plates contain a glucuronidase activity indicator, which can enable identification of a coliform colony as being $E.\ coli$ (for example, when formation of a blue precipitate is observed). Other culture devices, however, can provide only a provisional identification. When such a provisional identification is made, occasionally it can be desirable to confirm the identity of the coliform by performing additional tests. Thus, the process of the invention can include one or more additional, confirmatory tests, if desired.

After the culture device has been incubated and the presence of at least one coliform strain has been optically detected (for example, either visually or by an automated detection system), the captured microorganisms can be removed from the culture device for further confirmatory analysis or, in the case of certain genetic or immunological tests, the confirmatory analysis can be performed in the culture device (that is, in situ). Further confirmatory analysis can include chemical analyses (for example, chromatography, spectroscopy, or spectrometry), genetic analysis (for example, hybridization or nucleic acid amplification), and/or immunological analysis (for example, enzyme-linked immunosorbent assay (ELISA), immunochromatography, agglutination, or radial immunoassay).

The confirmatory analytical methods can be performed using the entire sample in the culture device by, for example, removing or extracting the microorganisms or components thereof from the particulate concentration agent and the culture medium. Alternatively, smaller regions of the culture device or individual colonies can be isolated and/or extracted to perform the confirmatory analytical methods. In some methods, a nitrocellulose or nylon membrane can be used to "lift" the microorganisms or components thereof and subsequently perform genetic, biochemical, or immunological tests. Specific confirmatory analytical methods can be found in *Molecular Cloning, A Laboratory Manual*, $3^{rd}$ Edition (Cold Spring Harbor Laboratory Press, Cold Spring Harbor, N.Y.), the descriptions of the methods being incorporated herein by reference.

Diagnostic Kit

Culture device(s) and particulate concentration agent(s) can be combined with packaging material and sold as a diagnostic (or sample testing) kit for detecting the coliforms present in a sample. Such a kit for use in carrying out the process of the invention comprises (a) at least one culture device comprising at least one culture medium that is hydrated or hydratable; and (b) at least one particulate concentration agent that is substantially optically transparent when in contact with the culture medium in the culture device when the culture medium is hydrated.

Preferably, the culture device of the kit comprises culture medium that comprises at least one fermentable nutrient (more preferably, the culture device is a flat film culture device comprising culture medium that comprises at least one fermentable nutrient), and/or the particulate concentration agent comprises microparticles (more preferably, inorganic microparticles). The diagnostic kit preferably further comprises one or more components selected from testing containers (more preferably, sterile testing containers), lysis reagents, buffers, optical detection assay components (for example, one or more indicator dyes), instructions for using the particulate concentration agent and/or the culture device in carrying out the process of the invention, an automated detection system (for example, a hand-held detection device or reader), and combinations thereof.

The particulate concentration agent optionally can be hydrated in a small volume of buffer with preservative to improve stability during storage and transportation and/or can be contained/aliquotted in a tear-open, sealed pouch to prevent contamination. The particulate concentration agent can be in the form of a dispersion or suspension in a liquid or can be in powder form. Preferably, the diagnostic kit comprises pre-measured aliquots (for example, based upon sample volume) of particulate concentration agent (more preferably, contained in one or more tear-open, sealed pouches).

The kit can further comprise sampling and/or testing accessories, such as a sample suspending medium (for example, water, buffer, or growth medium), a reagent (for example, a dye, an indicator, an enzyme, an enzyme substrate, a lysing agent, or a reagent to facilitate elution), a sampling device (which can optionally comprise particulate concentration agent and/or buffer), a pipette, a label, forceps, a sample carrier, and/or a glove. The individual components of the kit can be sterilized and/or can be in individually-wrapped primary packaging, if desired.

EXAMPLES

Objects and advantages of this invention are further illustrated by the following examples, but the particular materials and amounts thereof recited in these examples, as well as other conditions and details, should not be construed to unduly limit this invention. All parts, percentages, ratios, and so forth, in the following examples are by weight, unless noted otherwise. All microorganism cultures were purchased from The American Type Culture Collection (ATCC; Manassas, Va.). Solvents and other reagents were obtained from Sigma-Aldrich Chemical Company, Milwaukee, Wis., unless specified differently.

Preparation of Surface-Modified Diatomaceous Earth Particulate Concentration Agents Kieselguhr (diatomaceous earth) was purchased from Alfa Aesar (A Johnson Matthey Company, Ward Hill, Mass.) as a white powder (325 mesh; all particles less than 44 micrometers in size). This material was shown by X-ray diffraction (XRD) to contain amorphous silica along with crystalline α-cristobalite and quartz.

Particulate concentration agents comprising two different surface modifiers (namely, titanium dioxide and ferric oxide) were prepared by surface treating the diatomaceous earth in the manner described below:

Deposition of Titanium Dioxide

A 20 weight percent titanium (IV) oxysulfate dehydrate solution was prepared by dissolving 20.0 g of TiO$(SO_4) \cdot 2H_2O$ (Noah Technologies Corporation, San Antonio, Tex.) in 80.0 g of deionized water with stirring. 50.0 g of this solution was mixed with 175 mL of deionized water to form a titanium dioxide precursor compound solution. A dispersion of diatomaceous earth was prepared by dispersing 50.0 g of diatomaceous earth in 500 mL of deionized water in a large beaker with rapid stirring. After heating the diatomaceous earth dispersion to about 80° C., the titanium dioxide precursor compound solution was added dropwise while rapidly stirring over a period of about 1 hour. After the addition, the beaker was covered with a watch glass and its contents heated to boiling for 20 minutes. An ammonium hydroxide solution was added to the beaker until the pH of the contents was about 9. The resulting product was washed by settling/decantation until the pH of the wash water was neutral. The product was separated by filtration and dried overnight at 100° C.

A portion of the dried product was placed into a porcelain crucible and calcined by heating from room temperature to 350° C. at a heating rate of about 3° C. per minute and then held at 350° C. for 1 hour.

Deposition of Iron Oxide

Iron oxide was deposited onto diatomaceous earth using essentially the above-described titanium dioxide deposition process, with the exception that a solution of 20.0 g of $Fe(NO_3)_3 \cdot 9H_2O$ (J. T. Baker, Inc., Phillipsburg, N.J.) dissolved in 175 mL of deionized water was substituted for the titanyl sulfate solution. A portion of the resulting iron oxide-modified diatomaceous earth was similarly calcined to 350° C. for further testing.

Materials 18 megaohm water: 18 megaohm sterile deionized water obtained by using a Milli-Q™ Gradient deionization system from Millipore Corporation, Bedford, Mass.

3M™ Petrifilm™ E. coli/Coliform Count Plates (flat film culture devices comprising at least one fermentable nutrient) were obtained from 3M Company, St. Paul, Minn.

Amine-functionalized glass beads having a size range of 30-50 microns were obtained from PolySciences, Inc., Warrington, Pa.

$CaCO_3$: calcium carbonate particles with a diameter range of 2.5-10 microns were obtained from Sigma-Aldrich, St. Louis, Mo.

CM-111: amorphous, spheroidized magnesium silicate; microspheres shaped as solid spheres with particle density of 2.3 g/cc; surface area of 3.3 m$^2$/g; particle size: 90 percent less than about 11 microns, 50 percent less than about 5 microns, 10 percent less than about 2 microns; obtained as 3M™ Cosmetic Microspheres CM-111 from 3M Company, St. Paul, Minn.

Fe-DE: ferric oxide deposited onto diatomaceous earth essentially as described above.

Hydroxyapatite: type-1 hydroxyapatite particles having particle sizes from 2-8 microns obtained from Sigma-Aldrich as catalog number H0252, St. Louis, Mo.

mHPA: hydroxyapatite-coated magnetic beads having a mean particle size of about 2 microns obtained from Chemicell, GmbH, Berlin, Germany.

PCTE-1: a polycarbonate track etch membrane filter with a mean pore size of about 0.4 microns obtained from Sterlitech, Kent, Pa.

PCTE-2: a polycarbonate track etch membrane filter with a mean pore size of about 0.2 microns (manufactured by Whatman; obtained from VWR, West Chester, Pa.).

Silica Microspheres: silicon dioxide microspheres having a mean diameter of about 2.5 microns; obtained from PolySciences, Inc., Warrington, Pa.

Ti-DE: titanium dioxide deposited onto diatomaceous earth essentially as described above.

Pre-Screening of Concentration Agents 100 mg of various particulate concentration agents (CM-111, $CaCO_3$, Ti-DE, hydroxyapatite, Fe-DE, and amine-functionalized glass beads) were weighed, added to 5 mL polypropylene tubes, and suspended in 1 mL of sterile deionized 18 megaohm water. 50 mg and 10 mg samples of Fe-DE were processed in the same manner. A volume of 200 microliters of Silica Microspheres and volumes of 100 microliters, 50 microliters, and 10 microliters of hydroxyapatite-coated magnetic beads (mHPA) were also processed in this manner. The tube contents were mixed by vortexing at top speed (setting 10: 3200 revolutions per minute (rpm)) for 10 seconds on a VWR Analog Vortex Mixer (VWR, West Chester, Pa.). The suspended particulate concentration agents were plated on the 3M™ Petrifilm™ E. coli/Coliform Count Plates and sealed according to the manufacturer's instructions. A 47 mm PCTE filter was wetted for about 2 minutes with sterile deionized water using a wash bottle and added to a 3M™ Petrifilm™ E. coli/Coliform Count Plate, which was then hydrated (by addition of about 1 mL of water around the edges and top of the filter) and sealed according to the manufacturer's instructions. The count plates (including a control plate comprising a sterile water sample without concentration agent) were analyzed by digital optical imaging using a 3M™ Petrifilm™ Plate Reader (PPR, 3M Company, St. Paul; automated optical detection system comprising at least one scanner) to obtain images. The images were further analyzed for signal in the blue, green and red channels of the PPR by using Image Pro Plus™ version 6.3.0.512 software by Media Cybernetics, Inc. (Bethesda, Md.).

The signal in the green channel of the PPR, which had a wavelength of 525 nm, was calculated as the sum of (green) light reflected from the top of the count plate and the (green) light transmitted from the back of the count plate. The data for light/signal transmission for the green channel of the PPR is shown in Table 1 below.

TABLE 1

| Particulate Concentration Agent | Percent Signal Transmission in Green Channel |
|---|---|
| Control (Water Only) | 100 |
| CM-111 | 114 |
| CaCO$_3$ | 98 |
| Ti-DE | 95 |
| Hydroxyapatite | 76 |
| Silica Microspheres | 119 |
| Fe-DE (100 mg) | 11 |
| Fe-DE (50 mg) | 25 |
| Fe-DE (10 mg) | 66 |
| Amine-Functionalized Glass Beads | 110 |
| mHPA (100 μL) | 43 |
| mHPA (50 μL) | 58 |
| mHPA (10 μL) | 80 |
| PCTE-1 Filter | 71 |
| PCTE-2 Filter | 90 |

Examples 1-7 and Comparative Examples C-1-C-5

A loopful (standard four millimeter bacteriological loop) of overnight streaked culture of *E. coli* (ATCC 51813) from a Tryptic Soy Agar plate (Becton Dickinson, Sparks, Md.) was used to make a 0.5 McFarland standard (Vitek DENSICHEK, bioMerieux, Inc., Durham, N.C.) in 3 mL Butterfield's Buffer (pH 7.2, VWR, West Chester, Pa.). This standard corresponded to ~$10^8$ colony forming units/mL (CFU/mL). Serial dilutions were made in filter-sterilized deionized 18 megaohm water. A 1:1000 further dilution from a $10^2$ CFU/mL dilution was carried out in 100 mL of filter-sterilized 18 megaohm water, resulting in a final concentration of 0.1 CFU/mL (10 CFUs total). A 1 mL aliquot of a 100× strength Adsorption Buffer (pH 7.2; 1× strength containing 5 mM KCl, 1 mM CaCl$_2$, 0.1 mM MgCl$_2$, and 1 mM K$_2$HPO$_4$ per liter of water) was added to get a final concentration of 1×.

Particulate concentration agents were weighed in the amounts set forth above (under Pre-Screening of Concentration Agents) and added to 250 mL sterile polypropylene conical bottom tubes (VWR, West Chester, Pa.). The tubes were capped and their contents mixed by shaking manually at room temperature (25° C.) for about 1 minute.

After mixing, the tubes were incubated for 45 minutes on a Thermolyne Vari Mix™ rocking platform (Barnstead International, Iowa, 14 cycles/minute). After the incubation, the tube contents were divided into 2×50 mL sterile, conical polypropylene tubes (VWR, West Chester, Pa.) and centrifuged at 2500 rpm for 5 minutes to segregate the resulting *E. coli*-bound particulate concentration agent. The resulting supernatant was decanted off, the *E. coli*-bound particles of concentration agent were resuspended in 1 mL Butterfield's Buffer and plated on 3M™ Petrifilm™ *E. coli*/Coliform Count Plates.

The resulting *E. coli*-bound hydroxyapatite-coated magnetic beads (mHPA) were segregated and separated using a magnet (3-in-1 Magnetic Particle Separator, CPG, Inc., Lincoln Park, N.J.) for 5 minutes and plated as above. Each count plate was sealed according to the manufacturer's instructions and incubated in a 37° C. incubator (VWR Orbital Shaking Incubator, Model #1575R, West Chester, Pa.).

A 1:1000 dilution from the initial $10^2$ CFU/mL (without particulate concentration agent) was plated as a control on 3M™ Petrifilm™ *E. coli*/Coliform Count Plates.

Two 47 mm filters (PCTE-1 and PCTE-2) were tested by placing each filter in a sterilized glass filtration apparatus. Two 100 mL water samples containing about 10 CFUs *E. coli* were prepared (essentially as described above), and a sample was passed through each filter by using negative pressure (vacuum). The filters were removed by a surface-sterilized pair of forceps and placed on 3M™ Petrifilm™ *E. coli*/Coliform Count Plates, which were then hydrated essentially as described above and sealed according to the manufacturer's instructions. The filter-containing count plates were incubated overnight in a 37° C. incubator.

Colony counts were obtained in situ (that is, without separating the *E. coli* from the concentration agent) by first using a 3M™ Petrifilm™ Plate Reader (automated optical detection) and then by human visual inspection (manual optical detection) as a check of the automated reader counts. Results were calculated by using the following formula (and by averaging the automated and manual colony counts):

Capture Efficiency=(Number of Colonies on Concentration Agent/Total Number of Colonies in Control)×100

The results are shown in Table 2 below.

TABLE 2

| Example Number | Concentration Agent | Capture Efficiency (Percent) from 100 mL Water Sample (percent standard deviation, σ) |
|---|---|---|
| 1 | CM-111 | 87 |
| 2 | CaCO$_3$ | 92 * |
| 3 | Ti-DE | 84 (σ = 13) |
| 4 | Hydroxyapatite | 90 |
| 5 | Silica Microspheres | 106 |
| C-1 | Fe-DE (100 mg) | 93 (σ = 11) |
| C-2 | Fe-DE (50 mg) | 60 |
| 6 | Fe-DE (10 mg) | 37 |
| 7 | Amine-Functionalized Glass Beads | 30 (σ = 14) |
| C-3 | mHPA (100 μL) | 100 ** |
| C-4 | PCTE-1 Filter | 100+ *** |
| C-5 | PCTE-2 Filter | 40 |

\* σ = 11 for control
\*\* σ = 15 for control
\*\*\* σ = less than 15 for control Example 8 and Comparative Examples C-6 and C-7

An overnight growth of *E. coli* was used to make a 0.5 McFarland standard essentially as described above. The particulate concentration agent CM-111 was tested for capture of ~10 CFUs *E. coli* from a 50 mL water sample essentially as described above. The time of contact between the CM-111 and the sample was 30 minutes, and the resulting *E. coli*-bound CM-111 was segregated and separated essentially as described above, to provide a pellet. The pellet was plated on a 3M™ Petrifilm™ *E. coli*/Coliform Count Plate and incubated essentially as described above. Control count plates containing ~10 CFUs and ~100 CFUs *E. coli* (without CM-111) were also processed similarly (as Comparative Examples C-6 and C-7, respectively). After incubation for 24 hours, the count plates were placed into a 3M™ Petrifilm™ Plate Reader (PPR, 3M Company, St. Paul; automated optical detection system), and the number of *E. coli* colonies was determined (in situ as described above) by the automated detection system or reader according to the manufacturer's instructions. The results are shown in Table 3 below, which includes replicate values separated by semicolons (two separate trials were carried out for each example).

A typical *E. coli* colony appeared in the count plates as a blue colony with a proximate gas bubble. The last column in Table 3 shows the number of colonies that were miscounted by the image analysis software of the PPR, based upon a check by human visual inspection (manual optical detection). Apparently relatively large gas bubbles sometimes caused the automated detection system to count a single colony as 2 or 3 colonies, depending upon the size of the bubble.

TABLE 3

| Example Number | CFUs Blue With Gas Bubble (Automated) | CFUs Blue Without Gas Bubble (Automated) | CFUs Red With Gas Bubble (Automated) | CFUs Red Without Gas Bubble (Automated) | CFUs Miscounted by Automated Reader (Manual Check) |
|---|---|---|---|---|---|
| C-7 | 82; 95 | 0; 0 | 12; 2 | 0; 0 | 12; 2 |
| C-6 | 8; 9 | 0; 0 | 0; 0 | 0; 0 | 0; 0 |
| 8 | 8; 8 | 0; 0 | 6; 1 | 0; 0 | 6; 1 |

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

I claim:

1. A process for detecting the presence of at least one coliform strain comprising
   (a) providing at least one sample suspected of comprising at least one coliform strain;
   (b) providing at least one culture device comprising at least one culture medium that is hydrated or hydratable;
   (c) providing at least one particulate concentration agent that is substantially optically transparent when in contact with said culture medium in said culture device when said culture medium is hydrated, wherein said particulate concentration agent is amorphous, spheroidized magnesium silicate;
   (d) placing said particulate concentration agent in contact with said sample such that at least a portion of said coliform strain is bound to or captured by said particulate concentration agent to form coliform-bound particulate concentration agent;
   (e) placing said coliform-bound particulate concentration agent in contact with said culture medium of said culture device;
   (f) incubating said culture device comprising said coliform-bound particulate concentration agent in contact with said culture medium, said culture medium being hydrated; and
   (g) optically detecting the presence of said coliform strain without separating said coliform strain from said particulate concentration agent.

2. The process of claim 1, wherein said sample is in the form of a fluid.

3. The process of claim 1, wherein said sample is a water sample.

4. The process of claim 1, wherein said coliform strain is a gas-producing coliform strain.

5. The process of claim 1, wherein said coliform strain is *Escherichia coli*.

6. The process of claim 1, wherein said culture medium comprises at least one fermentable nutrient.

7. The process of claim 1, wherein said culture device is a flat film culture device comprising culture medium that comprises at least one fermentable nutrient.

8. The process of claim 1, wherein said particulate concentration agent captures or binds at least about 60 percent of the microorganisms present in said sample, relative to a corresponding control sample without said particulate concentration agent.

9. The process of claim 1, wherein said placing in contact with said sample is carried out by mixing said particulate concentration agent and said sample.

10. The process of claim 1, wherein said process further comprises segregating said coliform-bound particulate concentration agent and/or separating the resulting segregated particulate concentration agent from said sample.

11. The process of claim 1, wherein said process further comprises identifying and/or enumerating said coliform strain.

12. The process of claim 1, wherein said optically detecting comprises detecting at least one color change.

13. The process of claim 1, wherein said optically detecting is effected by an automated optical detection system.

14. A process for detecting the presence of *Escherichia coli* comprising
   (a) providing at least one water sample suspected of comprising *Escherichia coli*;
   (b) providing at least one flat film culture device comprising at least one culture medium that is hydrated or hydratable and that comprises at least one fermentable nutrient;
   (c) providing at least one particulate concentration agent that is substantially optically transparent when in contact with said culture medium in said flat film culture device when said culture medium is hydrated, said particulate concentration agent comprising amorphous, spheroidized magnesium silicate;
   (d) placing said particulate concentration agent in contact with said water sample such that at least a portion of said *Escherichia coli* is bound to or captured by said particulate concentration agent to form *Escherichia coli*-bound particulate concentration agent;
   (e) placing said *Escherichia coli*-bound particulate concentration agent in contact with said culture medium of said flat film culture device;

(f) incubating said flat film culture device comprising said *Escherichia coli*-bound particulate concentration agent in contact with said culture medium, said culture medium being hydrated; and (g) optically detecting the presence of said *Escherichia coli* without separating said *Escherichia coli* from said particulate concentration agent, said optically detecting comprising detecting at least one color change and the presence of at least one gas bubble proximate at least one *Escherichia coli* colony by digital optical imaging using an automated optical detection system comprising at least one scanner.

\* \* \* \* \*